(12) United States Patent
Heller

(10) Patent No.: US 6,274,786 B1
(45) Date of Patent: Aug. 14, 2001

(54) ANTI-REFLUX/HEARTBURN DEVICE

(76) Inventor: Brian Heller, 15 Abington Square, Apt. #26, New York, NY (US) 10014

( * ) Notice: Subject to any disclaimer, the term of this patent is extended or adjusted under 35 U.S.C. 154(b) by 0 days.

(21) Appl. No.: 09/066,257

(22) Filed: Apr. 27, 1998

(51) Int. Cl.[7] .................................................. A61F 13/00
(52) U.S. Cl. ............................... 602/41; 602/42; 602/60; 128/888; 128/889
(58) Field of Search ............................... 606/201–204.25; 602/41–59; 128/888, 889, 893, 894; 601/132–134, 118–123; D24/200, 211, 214

(56) References Cited

U.S. PATENT DOCUMENTS

| | | |
|---|---|---|
| 2,547,727 | 4/1951 | Zaras . |
| 2,645,221 | 7/1953 | Carter . |
| 3,578,773 | 5/1971 | Schultz . |
| 4,592,342 | 6/1986 | Salmasian . |
| 4,787,379 | 11/1988 | Yeh . |
| 5,010,902 | 4/1991 | Rambo et al. . |
| 5,127,422 * | 7/1992 | Colon ................................... 128/870 |
| 5,275,384 * | 1/1994 | Onotsky ............................... 206/441 |
| 5,310,402 | 5/1994 | Rollband . |
| 5,643,315 * | 7/1997 | Daneshvar ........................... 606/201 |
| 5,848,981 * | 12/1998 | Herbranson ......................... 601/134 |

* cited by examiner

Primary Examiner—Kim M. Lewis
(74) Attorney, Agent, or Firm—Hoffman, Wasson & Gitler

(57) ABSTRACT

The device has a protrusion maintaining sustained pressure to an area of the upper abdomen. This mechanical pressure serves to assist in closing the cardiac sphincted, help induce esophageal relaxation and, in the case of a hiatal hernia, to return the stomach to the correct anatomical position. The device is semirigid to allow the device to apply pressure to the user without being pushed outwardly.

18 Claims, 9 Drawing Sheets

US 6,274,786 B1

ANTI-REFLUX/HEARTBURN DEVICE

BACKGROUND OF THE INVENTION

Many people suffer from gastroesophageal reflux disorder (GERD). Gastroesophageal reflux disorder is a reflux, or backward or return flow, of fluid of gastric or intestinal contents into the esophagus. Heartburn is a symptom of this disorder.

This condition arises when the lower esophageal sphincter, between the stomach and esophagus, becomes lax or spastic. This allows gastric acid to move from the stomach into the esophagus. The gastric juices irritate the esophagus lining.

Possible causes of the disorder include scleroderma, pregnancy, improper diet, autoimmune disorders or a hiatal hernia. Treatment for this disorder typically includes a change in diet and the use of non-prescription antacids or prescription medications. Severe cases may require anti-reflux surgery. Recurrence is common.

It is therefore an object of the invention to provide relief for gastroesophageal reflux disorder, in particular gastroesophageal reflux disorder caused by a hiatal hernia.

It is another object of the invention to provide a low cost treatment for gastroesophageal reflux disorder.

It is a further object of the invention to provide a device that closes the cardiac sphincter, aids the stomach in lowering away from and out of the esophageal hiatus and aids in esophageal relaxation.

It is still another object of the invention to provide a device that corrects and possibly prevents a hiatal hernia by applying sustained pressure on the stomach.

It is a further object of the invention to treat gastroesophageal reflux disorder in a non-chemical, non-surgical manner.

It is a further object of the invention to provide a cure for GERD that is both simple to use and inexpensive.

SUMMARY OF THE INVENTION

Chiropractors treat hiatal hernias by manually pressing down on the patient's abdomen. This mechanical pressure serves to return the stomach to its correct position, assist in closing the cardiac sphincter and help induce esophageal relaxation. The invention is a bandage having a protrusion that creates and maintains pressure on the stomach. The bandage maintains the protrusion in a position where it is applying pressure to the user's abdomen. For the relief of GERD, and hiatal hernias in particular, the device is applied to an area immediately to the right or left of the solar plexus, by the rib cage. This area is by the esophageal/gastric junction where the symptoms of GERD are felt.

The bandage has a semirigid portion allowing the protrusion to apply pressure. If the bandage did not have the semirigid portion, it would be pushed outwardly, and no pressure would be maintained. The semi-rigid portion is an endoskeleton of semi-rigid material that is sandwiched between pieces of a gauze-like material. The protrusion is a semidense plastic foam attached to the endoskeleton. Both the protrusion and endoskeleton are placed between layers of the gauge-like material.

DETAILED DESCRIPTION OF THE INVENTION

Figure 1:
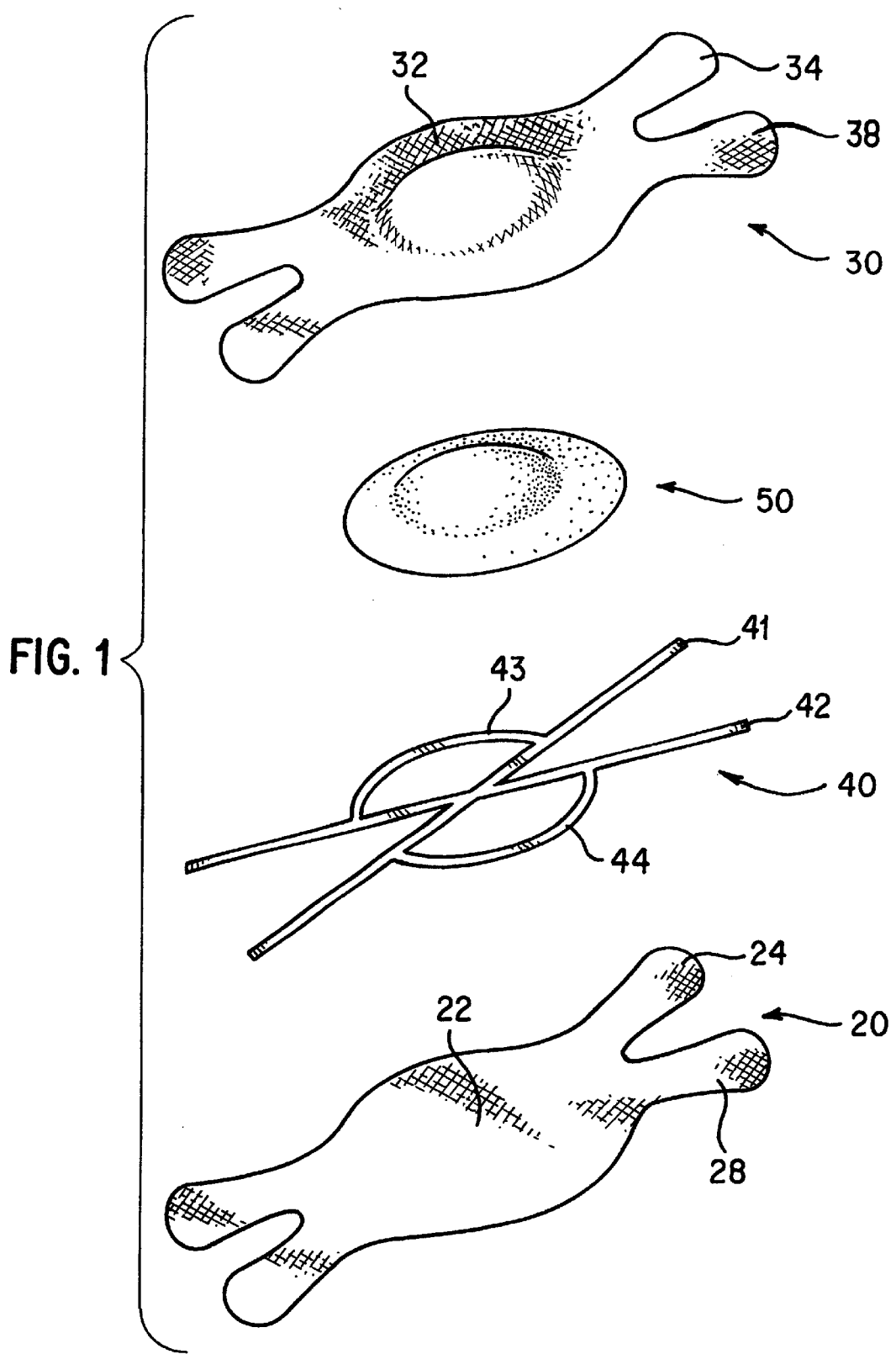
FIG. 1 is an exploded view of the bandage of the invention.

The invention can be better understood with reference to the drawings. FIG. 1 shows an exploded view of the components that make up the invention. The bandage has an outer layer 20 with a middle portion 22 and a pair of upper end pieces 24 and lower end pieces 28. An endoskeleton 40 provides rigidity to the invention. The endoskeleton, in this embodiment, has a first diagonal strut 41 and a second diagonal strut 42. The endoskeleton also has an upper strut 43 and a lower strut 44. The upper and lower struts are slightly arcuate.

A protrusion 50 is positioned on top of the endoskeleton 40. This protrusion provide the pressure to the user's upper abdomen to achieve the desired results. The protrusion 50 is preferably made from semi-dense foam, however, any rigid material will serve the purpose. The protrusion and endoskeleton are covered by an inner layer 30. The inner layer is covered with adhesive to secure the bandage to the user. The inner layer has a shape identical to the outer layer 20. As shown in FIG. 1, the inner layer has a middle portion 32 and a pair of upper end pieces 34 and a pair of lower and pieces 38. The upper end pieces and lower end pieces of the bandage diverge from each other as they extend from the middle portion of the bandage.

Figure 2:
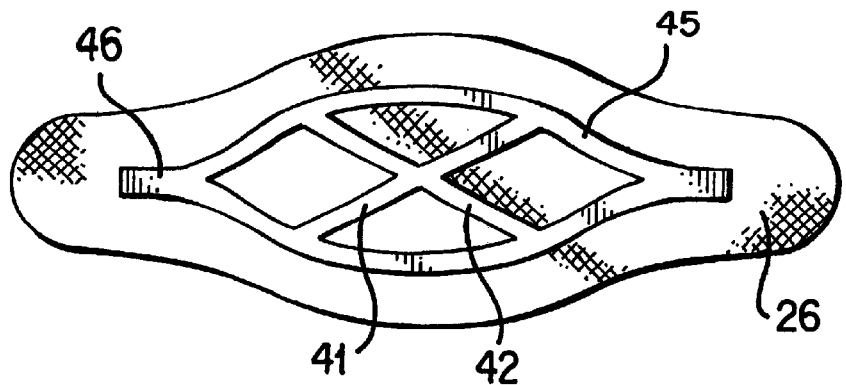
FIG. 2 is a top view of the outer layer and endoskeleton of a second embodiment of the bandage.

FIGS. 2 through 6 disclose other embodiments of the bandage. The Figures show only the outer covering and endoskeleton for purposes of clarity. The inner layer has an identical shape to the outer cover. In FIG. 2, the outer cover has only two end pieces 26, one on each side. The endoskeleton has a first diagonal piece 41 and second diagonal piece 42. There is an oval shaped strut 45 and an extension 46 for each end section of the outer cover. As can be seen, the diagonal struts 41, 42 do not extend out of the oval struts 45.

Figure 3:
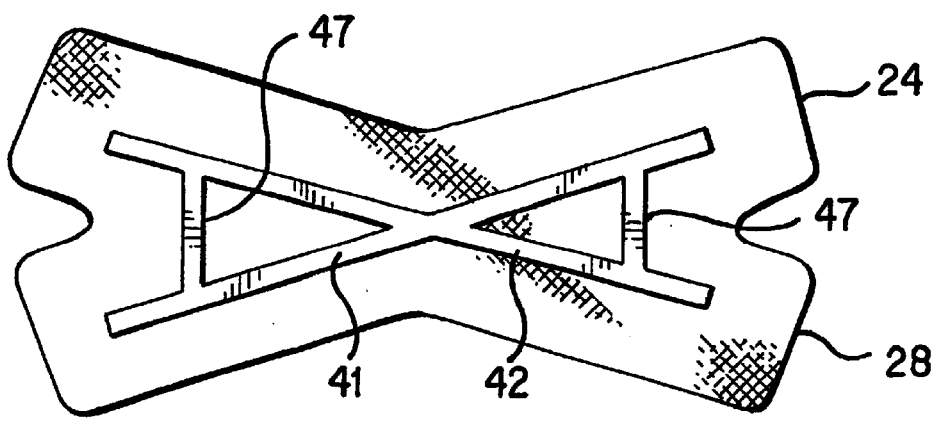
FIG. 3 is a top view of the outer layer and endoskeleton of a third embodiment.

FIG. 3 discloses another embodiment of the outer cover and endoskeleton. The outer cover has a general X shape. The endoskeleton is made up of a first diagonal piece 41 and a second diagonal piece 42. There are two vertical strut 47 running between the diagonal struts 41 and 42.

Figure 4:
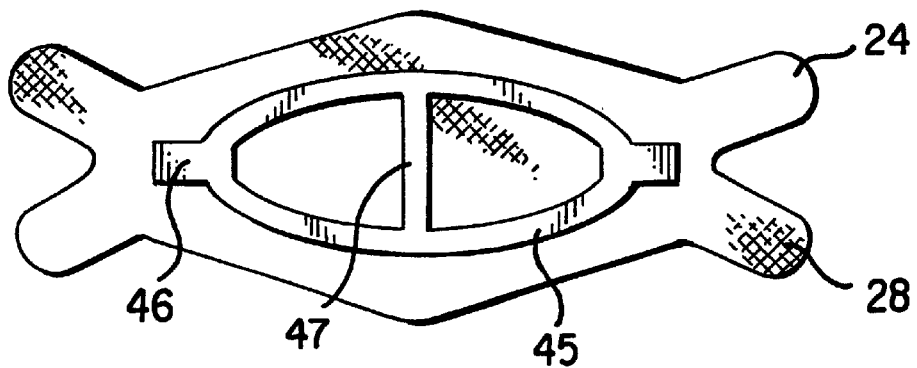
FIG. 4 is a top view of the outer layer and endoskeleton of a fourth embodiment.

FIG. 4 shows yet another embodiment of the invention. The outer layer has a general diamond shaped middle portion 22 and a pair of upper end pieces 24 and lower end pieces 28. The endoskeleton is made up of an oval strut 45 with two end sections 46 extending from the oval towards the end pieces. A single vertical strut 47 is located in approximately the middle of the oval.

Figure 5:
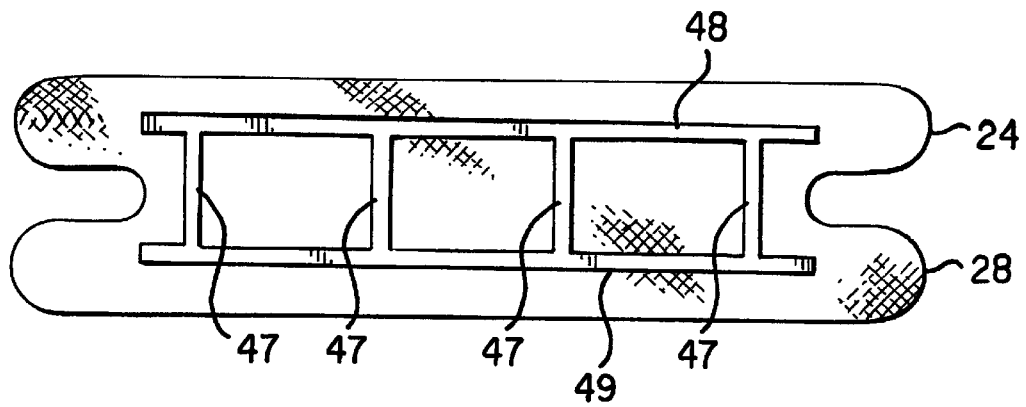
FIG. 5 is a top view of the outer layer and endoskeleton of a fifth embodiment.

FIG. 5 depicts an embodiment of the invention that has a generally rectangular middle portion and a pair of upper end pieces 24 and lower end pieces 28. The end pieces 24 and 28 are parallel to each other as they extend from the middle portion. The endoskeleton has an upper strut 48 and lower strut 49. These two struts also remain parallel to each other. They are connected by a series of vertical struts 47.

Figure 6:
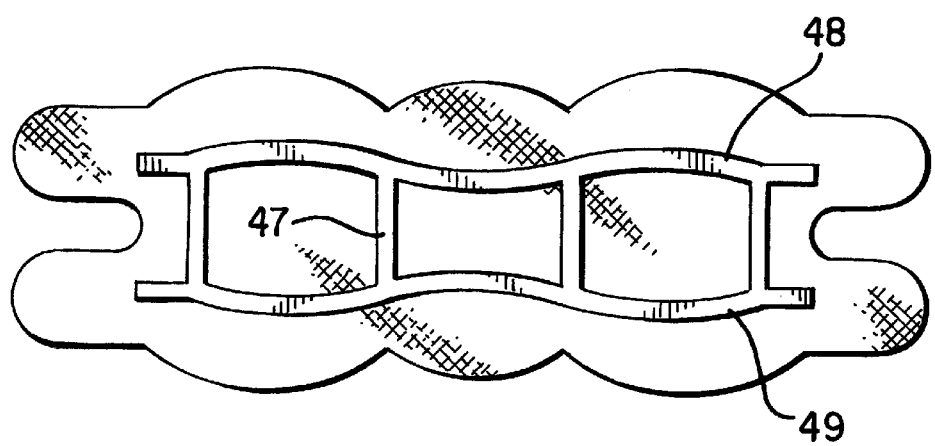
FIG. 6 is a top view of the outer layer and endoskeleton of a sixth embodiment.

FIG. 6 discloses another embodiment of the invention similar to that shown in FIG. 5. Similar to the embodiment of FIG. 5, the end pieces of the bandage 24, 28 remain parallel to each other as they extend from the middle portion. This embodiment has a middle portion with a upper and lower edge that is formed by three curves that intersect each other to create a somewhat sinusoidal profile. The upper strut 48 and lower strut 49 of the endoskeleton also have a slightly arcuate direction generally mirroring the edges of the outer layer 20. The upper and lower struts are joined by a series of vertical struts 47.

Figure 7:
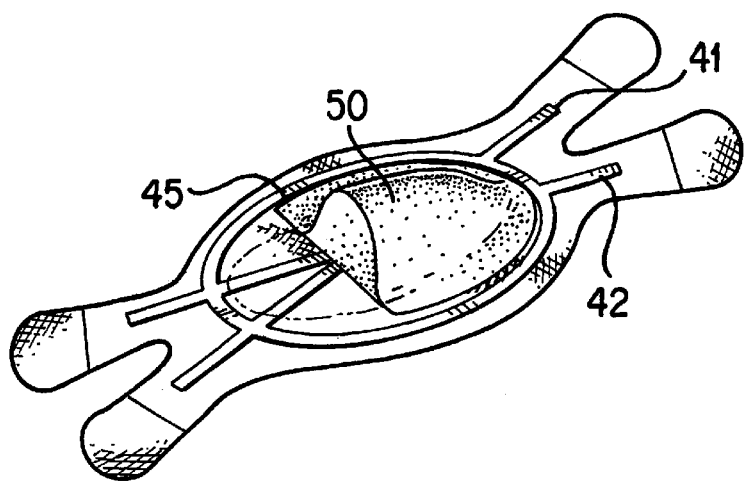
FIG. 7 is a view of the bandage and protrusion together with part of the protrusion cut away for purposes of clarity.

FIG. 7 depicts a bandage with its outer layer 20 removed and half of the protrusion removed to show detail. This bandage has a first diagonal strut 41, a second diagonal strut 42 and an oval strut 45. The figure shows half of the protrusion 50 and it can be seen how the protrusion is situated relative to the endoskeleton. Also, in this embodiment, the ends of the end pieces 24 and 28 are made of a material which has more elasticity than the gauze-like material of the outer layer 20.

Figure 8A:
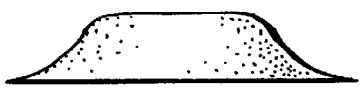
FIGS. 8A–G are side views of variation of the protrusion that is part of the invention.
Figure 8D:
Figure 8B:
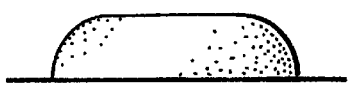
Figure 8E:
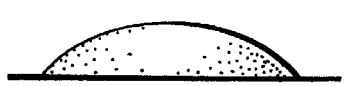
Figure 8C:
Figure 8F:
Figure 8G:
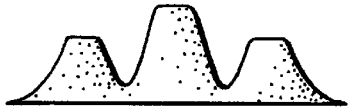
Figure 9A:
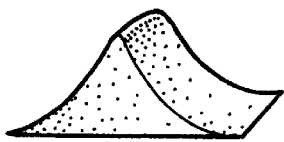
FIGS. 9A–F shows perspective view of cross sections of alternative protrusions.
Figure 9B:
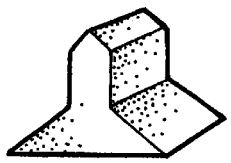
Figure 9C:
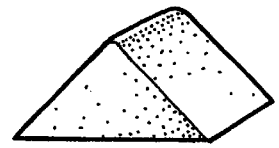
Figure 9D:
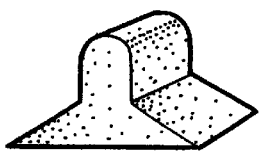
Figure 9E:
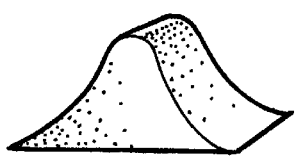
Figure 9F:
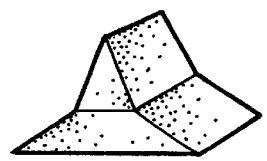

FIGS. 8A–G shows side views of various protrusions that can be used with the invention. FIGS. 8A through 8C disclose protrusions which have a flat top and curved sides. 8D and 8E disclose protrusions which have curved tops which extend down to the outer cover. FIGS. 8F and G disclose protrusions which have three separate peaks. FIGS. 9A–E disclose prospective views of cross-sections of alternate protrusions that can be used with the invention.

Figure 10:
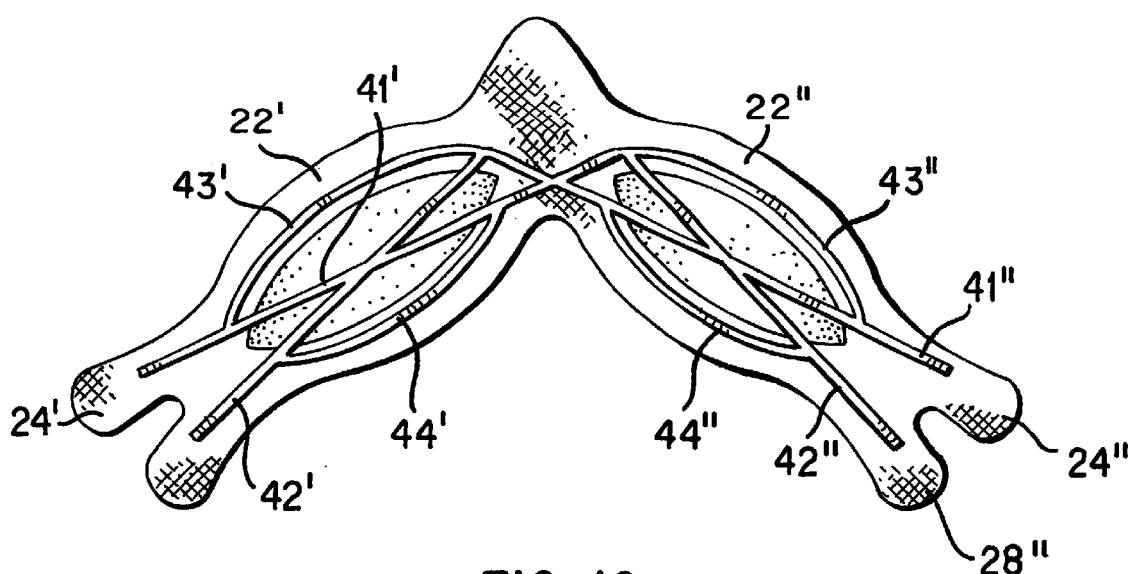
FIG. 10 is an embodiment of the invention having dual protrusions to create bilateral pressure.
Figure 11:
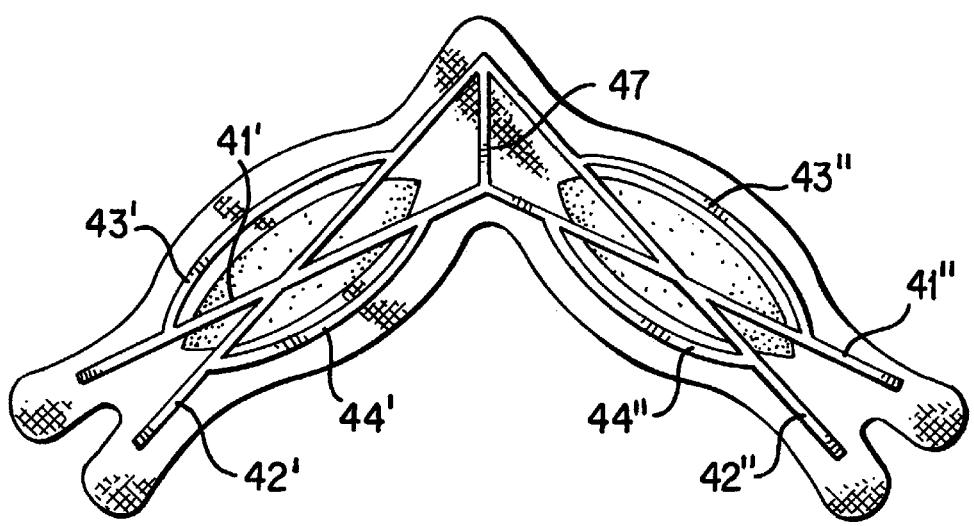
FIG. 11 is a variation of the embodiment shown in FIG. 9.

FIGS. 10 and 11 show an embodiment of the invention having dual protrusions. The bandage has first and second middle portions 22' and 22". Each middle portion has a upper end piece 24', 24" and a lower end piece 28', 28". The endoskeleton of each half is made of a first diagonal strut 41', 41" and a second diagonal strut 42', 42". There is also upper struts 43' and 43" and lower struts 44' and 44".

FIG. 11 discloses a modification of the embodiment having the dual protrusions. In this embodiment, the second diagonal strut 42' and 42" extend until they intersect. A vertical strut 47 extends from the point of intersection of the second diagonal struts 42', 42" to the point of intersection of the first diagonal struts 41', 41".

Figure 12A:
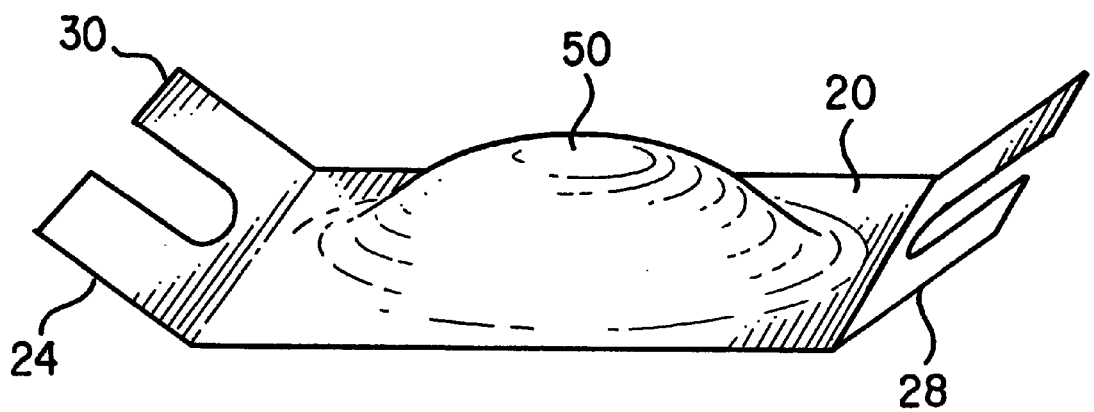
FIGS. 12A–B show the invention having a bent middle section.
Figure 12B:
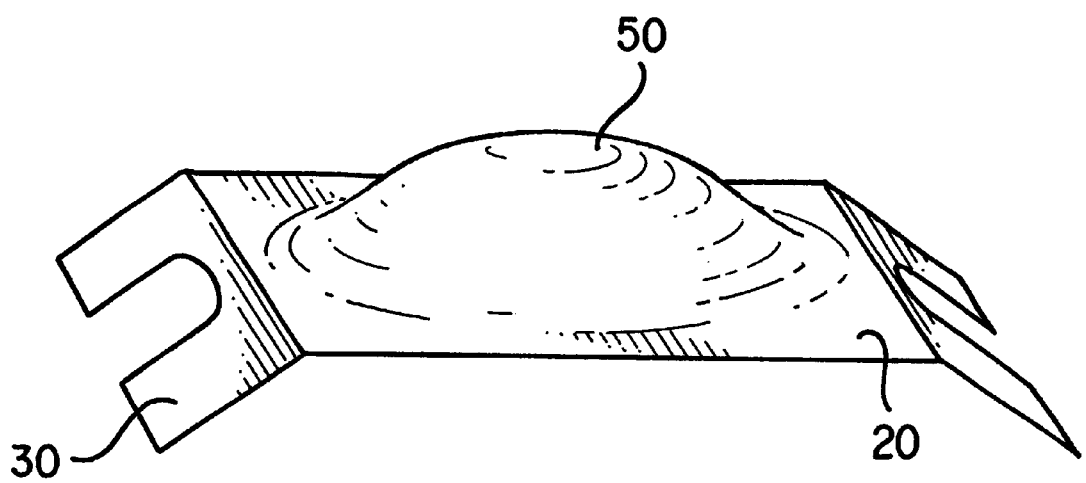

Turning now to FIGS. 12A and 12B, a slight modification of the bandage is shown. In this embodiment, the bandage has a middle section 22 with its left and right end pieces 24, 28 bent upwards or downwards at an angle. This is achieved by forming the endoskeleton 40 of rigid material having the bends in it. The endoskeleton 40 will then maintain the bandage in that position. When the middle section 22 beyond the protrusion are bent downward, the device pushes into the skin. The attachment of the end portions 24, 28 of the bandage to the skin maintains the device in its depressed position. This depression, in turn, causes pressure on the cardiac sphincter and the stomach.

Figure 13:
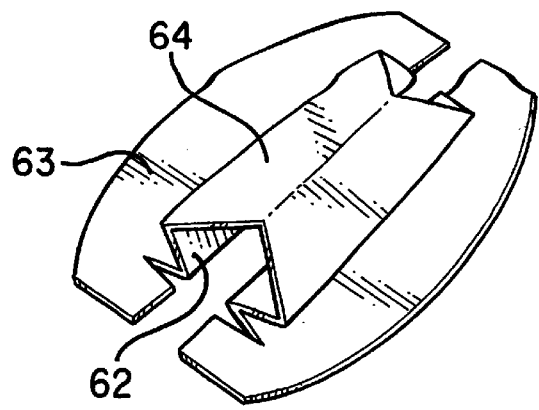
FIG. 13 discloses a one piece protrusion and endoskeleton.
Figure 14:
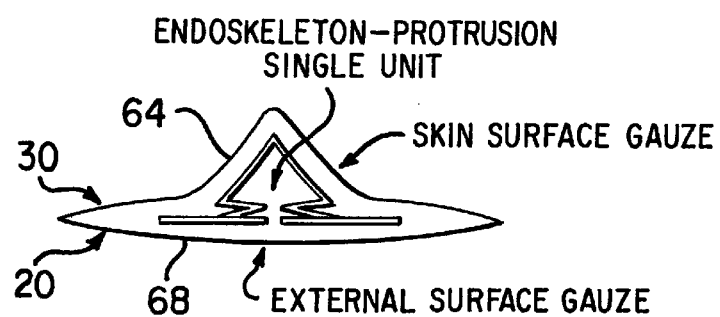
FIG. 14 is a cross section of the one piece protrusion and endoskeleton used in a bandage.

FIG. 13 discloses a one piece protrusion and endoskeleton 60. The one piece protrusion and endoskeleton has two base portions 68 separated from each other by a middle portion 69. Where the middle portion joins the base portion, there are cuts 61 extending into the base portion. The cut 61 allow the base portion in the proximity of the middle portion to rise out of the plane of the base portion. The middle portion 69 is split into four different panels 62, 64. The transition panel 62 are separated from the base portions 68 by a fold line 63 and from the peak panels 64 by a fold line 65. The peak panels are separated by a fold line 67 separating the two peak panels 64 from one another. When in the assembled form, the base portion 68 are co-planner and the transition panel 62 are folded back over the base portions 68. The peak panels extend from the transitional panels and converge towards each other at the fold line 67 to form a peak. It is the middle portion 69, with its transitional panels and peak panels, that forms the protrusion of the unit. FIG. 14 discloses the one piece protrusion and endoskeleton in a cross section of a bandage. As can be seen, the one piece protrusion and endoskeleton is enveloped between an outer cover 20 and inner cover 30.

Figure 15:
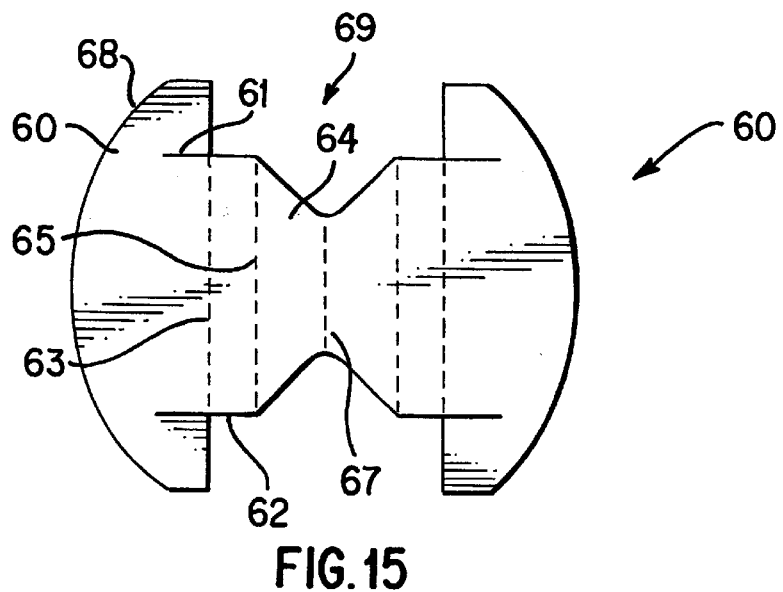
FIG. 15 shows the blank from which the one piece protrusion and endoskeleton is made.

FIG. 15 discloses the blank from which the one piece protrusion and endoskeleton is formed. The one piece protrusion and endoskeleton is cut from a piece of plastic or similar material such as cardboard and the cuts 61 and fold line 63, 65, 67 are formed. Once the blank is formed, it can be assembled, by machine or hand, to form an endoskeleton and protrusion. This assembled one piece protrusion endoskeleton can then be used in a bandage in accordance with the invention.

Figure 16:
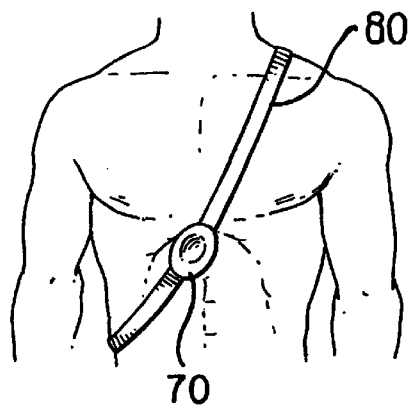
FIG. 16 shows a belt that can be used as part of the invention.
Figure 17:
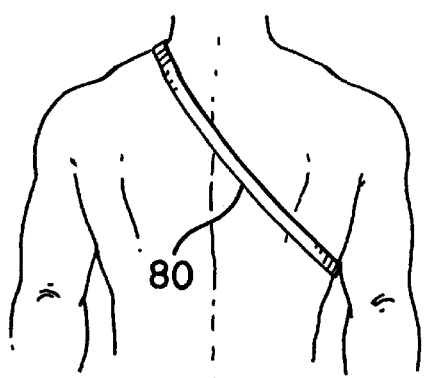
FIG. 17 shows the rear view of the belt of FIG. 14 being used.

FIG. 16 discloses a belt that can be used as part of the invention. The belt has a middle portion 70 having a protrusion. Pressure on the middle portions 70 is sustained by the tensioning of the belt 80. FIG. 17 discloses the rear view of a belt as it us used on a user.

Figure 18:
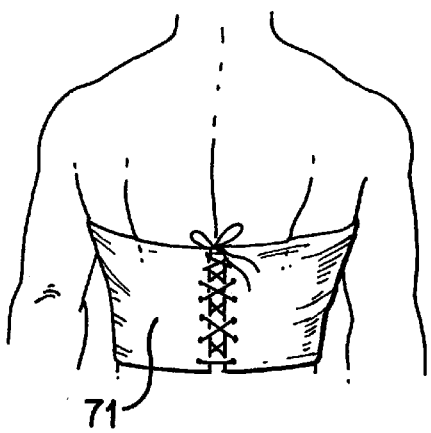
FIG. 18 shows a corset that can be used as part of the invention.

FIG. 18 discloses a corset 71 used in accordance with the invention. On the interior surface of the corset is a protrusion (not shown). The protrusion maintains pressure by tightening of the corset 71.

Figure 19:
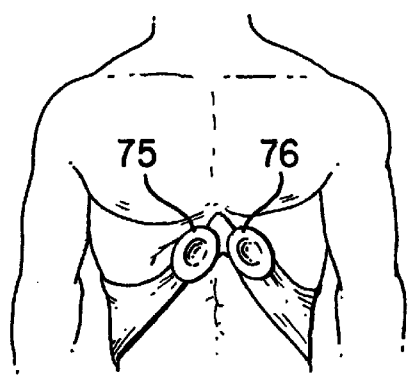
FIG. 19 shows a modified corset of FIG. 18 being used.

FIG. 19 discloses a modified corset which connects in the middle. The middle portion two protrusions 75, 76. This applies pressure to both sides of the abdomen.

Figure 20:
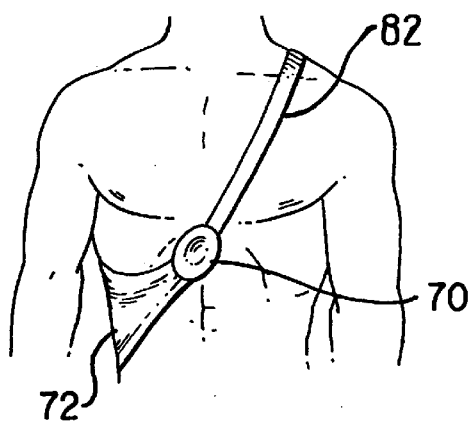
FIG. 20 shows a front view of a corset-belt that can be used as part of the invention.
Figure 21:
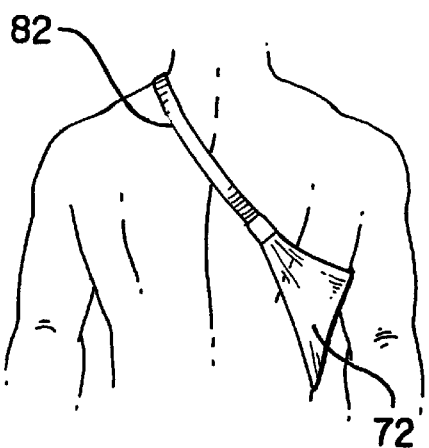
FIG. 21 shows a back view of the corset belt.

FIG. 20 discloses a corset-belt used in accordance with the invention. Similar to the other embodiments, the corset/belt has a middle section 70 having a protrusion. A corset portion 72 combined with a belt portion 82 serves to maintain pressure on the middle portion. FIG. 21 discloses a rear view of the corset/belt device.

Figure 22:
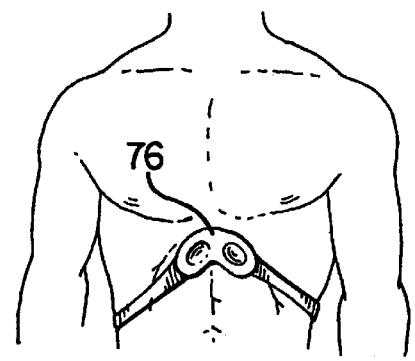
FIG. 22 is a belt that secures a dual protrusion device.
Figure 23:
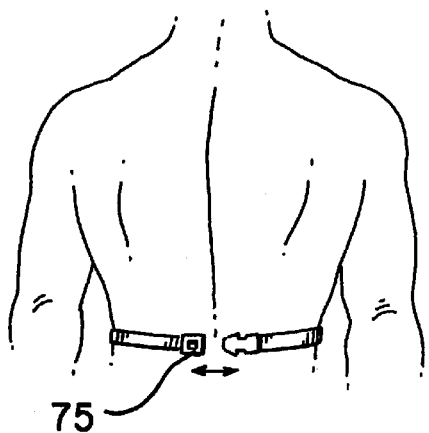
FIG. 23 is a rear view of the dual protrusion belt on a user.

FIG. 22 depicts a modified belt used with the invention. The belt has a middle portion 76 having dual protrusions. FIG. 23 shows a rear view of the modified belt including the connectors 75 used to secure the two ends of the belt to one another. Any releasable connector can be used to attach the two ends of the belt together.

Figure 24:
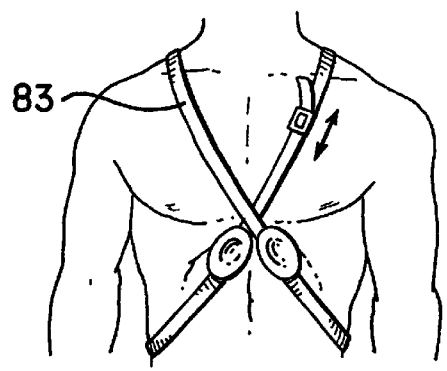
FIG. 24 depicts a dual protrusion harness having a belt around the back and a second belt around the neck.
Figure 25:
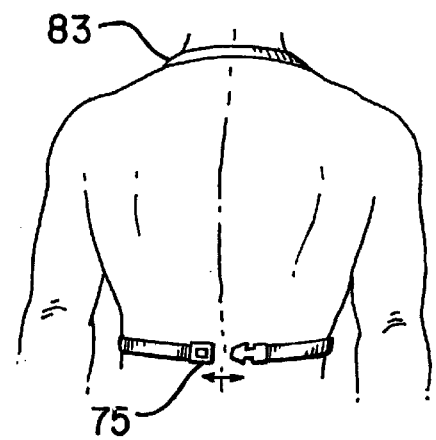
FIG. 25 shows a rear view of the harness of FIG. 24 on a user.

FIG. 24 shows a further modification of the embodiment of FIG. 22. In this embodiment, the middle portion having the dual protrusion 76 is connected to an adjustable strap that goes around the user's neck. The neck strap 83 has a means to adjust the length of the strap. FIG. 25 shows a rear view of this embodiment on a user.

Figure 26:
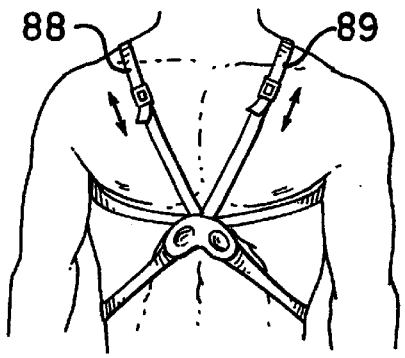
FIG. 26 shows a modification of the dual protrusion harness having a pair of shoulder straps.
Figure 27:
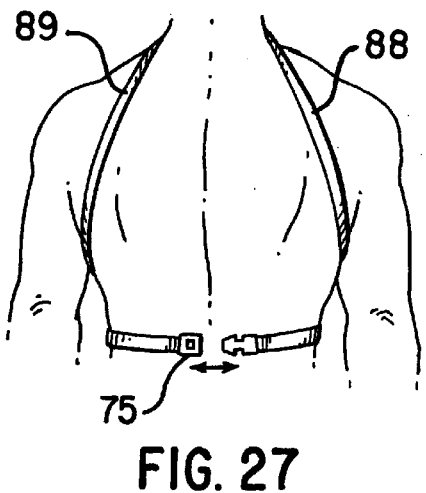
FIG. 27 shows a rear view of the harness of FIG. 26 on a user.

FIG. 26 discloses another embodiment of the modified belt of FIG. 22. In this instance, the middle portion having dual protrusions 76 is connected to pair of straps which secure around the shoulders of the user. Each of the shoulder straps 88, 89 has its own means to adjust the length of the strap. FIG. 27 depicts the rear view of this belt on a user.

As can be seen by the disclosure, the invention uses a protrusion attached to a bandage or other device allowing the protrusion to sustain pressure on the stomach or cardiosphincter between the esophagus and stomach. The device therefore achieves relief of gastroesophical reflux disorder. This relief comes in the form of a non-chemical/non-surgical device. As such, it represents an alternative to those people who suffer from this disorder and desire an alternative to the currently available methods of treatment.

Although the invention has been described according to the preferred embodiments, the foregoing description is not meant to be limiting in any way, and is meant to be protected by the appended claims. Certain modifications would be inherent to one of ordinary skill in the art without departing from the spirit and scope of the invention.

What is claimed is:

1. A bandage comprising:

an outer layer having a middle portion;

a layer made of semi-rigid material, said semi-rigid layer being an endoskeleton;

a protrusion on the semi-rigid layer to apply pressure, and an inner layer having adhesive to secure the bandage to a person, said inner layer covering said protrusion.

2. The bandage of claim 1 further comprising end pieces connected to the edge of the middle portion.

3. The bandage of claim 1 wherein the semi-rigid layer is oval.

4. The bandage of claim 1 wherein the middle portion is diamond shaped.

5. The bandage of claim 1 wherein the end pieces are elastic.

6. The bandage of claim 5 wherein there are four end pieces.

7. The bandage of claim 1 wherein the endoskeleton is an oval piece and two diagonal struts.

8. The bandage of claim 1 wherein the endoskeleton is two parallel horizontal struts and at least two parallel vertical struts.

9. The bandage of claim 1 wherein the protrusion is made of semi-rigid material.

10. The bandage of claim 1 wherein the semi-rigid portion has three sections, two of the sections making an angle the third section.

11. The bandage of claim 1 further comprising two protrusions.

12. The bandage of claim 1 wherein the protrusion and endoskeleton are formed from a one piece blank.

13. The bandage of claim 12 wherein the protrusion and endoskeleton one piece blank comprises two base portions connected to a middle portion by fold lines, the middle portion comprising four panels connected to one another by fold lines.

14. An anti-reflux device, comprising:

an outer layer;

a semi-rigid layer on said outer layer, said semi-rigid layer being an endoskeleton;

a protrusion having a bottom surface and a top surface, said bottom surface contacting said semi-rigid layer and said top surface being nonplanar;

an inner layer, said inner layer covering said protrusion; and means for attaching the device to a person.

15. The anti-reflux device of claim 14, wherein said means for attaching is adhesive on said inner layer.

16. The anti-reflux device of claim 14, wherein said means for attaching is a harness.

17. The anti-reflux device of claim 14, wherein said means for attaching is a belt.

18. The anti-reflux device of claim 14, wherein said means for attaching is a corset-belt.

* * * * *